US010151962B2

(12) United States Patent
Gladnick et al.

(10) Patent No.: US 10,151,962 B2
(45) Date of Patent: Dec. 11, 2018

(54) VARIABLE FOCAL LENGTH LENS SYSTEM WITH FOCUS MONITORING AND CONTROL

(71) Applicant: Mitutoyo Corporation, Kanagawa-ken (JP)

(72) Inventors: Paul Gerard Gladnick, Seattle, WA (US); Kim Atherton, Kirkland, WA (US)

(73) Assignee: Mitutoyo Corporation, Kanagawa-ken (JP)

( * ) Notice: Subject to any disclaimer, the term of this patent is extended or adjusted under 35 U.S.C. 154(b) by 279 days.

(21) Appl. No.: 15/280,501

(22) Filed: Sep. 29, 2016

(65) Prior Publication Data

US 2018/0088440 A1 Mar. 29, 2018

(51) Int. Cl.
*G02F 1/29* (2006.01)
*G02F 1/33* (2006.01)
(Continued)

(52) U.S. Cl.
CPC ........... *G02F 1/33* (2013.01); *G01N 21/8806* (2013.01); *G02B 27/0988* (2013.01);
(Continued)

(58) Field of Classification Search
CPC ..... G02F 1/33; G01N 21/8806; H04N 5/2352
See application file for complete search history.

(56) References Cited

U.S. PATENT DOCUMENTS 4,029,976 A 6/1977 Fish et al.
5,488,674 A * 1/1996 Burt .......................... G06T 5/50
345/639
(Continued)

FOREIGN PATENT DOCUMENTS

WO 89/02062 A1 3/1989

OTHER PUBLICATIONS

Bryll, "Multi-Level Image Focus Using a Tunable Lens in a Machine Vision Inspection System," U.S. Appl. No. 14/841,051, filed Aug. 31, 2015, 40 pages.
(Continued)

*Primary Examiner* — Jayanti K Patel
*Assistant Examiner* — Irfan Habib
(74) *Attorney, Agent, or Firm* — Seed IP Law Group LLP

(57) ABSTRACT

A variable focal length (VFL) lens system is provided including a tunable acoustic gradient (TAG) lens and an optical focus monitoring configuration for providing a focus monitoring signal that reflects a focus state with high accuracy and without significant latency. An input illumination pattern is transmitted through the TAG lens to provide a corresponding output illumination pattern that has a size and intensity that depends on the optical power of the TAG lens. An optical focus signal detector portion includes a filtering configuration and a focus photodetector that provides a focus output signal that varies in relation to the total light energy that the focus photodetector receives, wherein the filtering configuration receives the output illumination pattern and limits the amount of included focus detection light that reaches the focus photodetector. A focus monitoring signal is provided based on the focus output signal provided by the focus photodetector.

25 Claims, 9 Drawing Sheets

(51) Int. Cl.
*G01N 21/88* (2006.01)
*G02B 27/09* (2006.01)
*H04N 5/235* (2006.01)

(52) U.S. Cl.
CPC ......... *H04N 5/2352* (2013.01); *H04N 5/2353* (2013.01); *H04N 5/2354* (2013.01); *G02F 2001/294* (2013.01)

(56) References Cited

U.S. PATENT DOCUMENTS

| | | | |
|---|---|---|---|
| 5,790,710 A * | 8/1998 | Price | G01N 15/147 250/201.3 |
| 6,064,507 A | 5/2000 | Heflinger et al. | |
| 6,542,180 B1 | 4/2003 | Wasserman et al. | |
| 7,324,682 B2 | 1/2008 | Wasserman | |
| 7,454,053 B2 | 11/2008 | Bryll et al. | |
| 7,535,382 B2 | 5/2009 | Jansson | |
| 8,111,905 B2 | 2/2012 | Campbell | |
| 8,111,938 B2 | 2/2012 | Bryll et al. | |
| 8,213,022 B1 * | 7/2012 | Riza | G01B 11/026 356/495 |
| 8,515,294 B2 | 8/2013 | Britz | H04B 10/90 398/212 |
| 8,907,729 B2 | 12/2014 | Temporiti Milani et al. | |
| 9,060,117 B2 * | 6/2015 | Bryll | H04N 5/235 |
| 9,143,674 B2 * | 9/2015 | Gladnick | G01B 11/0608 |
| 9,312,954 B2 * | 4/2016 | Chen | H04B 10/11 |
| 9,568,606 B2 * | 2/2017 | Ikemoto | G01S 17/89 |
| 9,602,715 B2 * | 3/2017 | Gladnick | H04N 5/23212 |
| 9,726,876 B2 * | 8/2017 | Bryll | G02B 21/241 |
| 9,774,765 B2 * | 9/2017 | Bryll | H04N 5/2178 |
| 9,830,694 B2 * | 11/2017 | Bryll | G02B 3/0081 |
| 9,880,265 B2 * | 1/2018 | Schneider | G01S 7/4816 |
| 2006/0093205 A1 * | 5/2006 | Bryll | G06T 7/0004 382/152 |
| 2007/0036531 A1 * | 2/2007 | Tokunaga | G03B 7/10 396/69 |
| 2008/0063294 A1 * | 3/2008 | Burt | H04N 5/23212 382/255 |
| 2009/0034641 A1 | 2/2009 | Jansson | |
| 2011/0075151 A1 * | 3/2011 | Jeong | G01N 21/956 356/453 |
| 2011/0133054 A1 * | 6/2011 | Campbell | G01B 11/0608 250/201.2 |
| 2012/0095533 A1 * | 4/2012 | Wang | A61N 5/0613 607/89 |
| 2012/0098949 A1 * | 4/2012 | Knebel | G02B 21/002 348/79 |
| 2012/0194814 A1 * | 8/2012 | Wang | G01J 3/021 356/301 |
| 2012/0201114 A1 * | 8/2012 | Sano | G11B 7/1365 369/112.16 |
| 2014/0368726 A1 * | 12/2014 | Gladnick | G01B 11/0608 348/349 |
| 2015/0094599 A1 * | 4/2015 | Kim | G02B 15/00 600/476 |
| 2015/0145980 A1 * | 5/2015 | Bryll | G02B 21/241 348/79 |
| 2017/0061601 A1 * | 3/2017 | Bryll | G02B 3/0081 |
| 2017/0078549 A1 * | 3/2017 | Emtman | G02B 21/367 |
| 2017/0318216 A1 * | 11/2017 | Gladnick | G02B 7/006 |

OTHER PUBLICATIONS

Bryll, "Phase Difference Calibration in a Variable Focal Lenth Lens System," U.S. Appl. No. 15/145,682, filed May 3, 2016, 44 pages.
Bryll et al., "Chromatic Aberration Correction in Maging System Including Variable Focal Lengths Lens," U.S. Appl. No. 14/854,624, filed Sep. 15, 2015, 34 pages.
Mermillod-Blondin et al., "High-speed varifocal imaging with a tunable acoustic gradient index of refraction lens," *Optics Letters* 33(18):2146-2148, 2008.
Mitutoyo, "QVPAK 3D CNC Vision Measuring Machine," User's Guide, Version 7, Jan. 2003, 329 pages.

\* cited by examiner

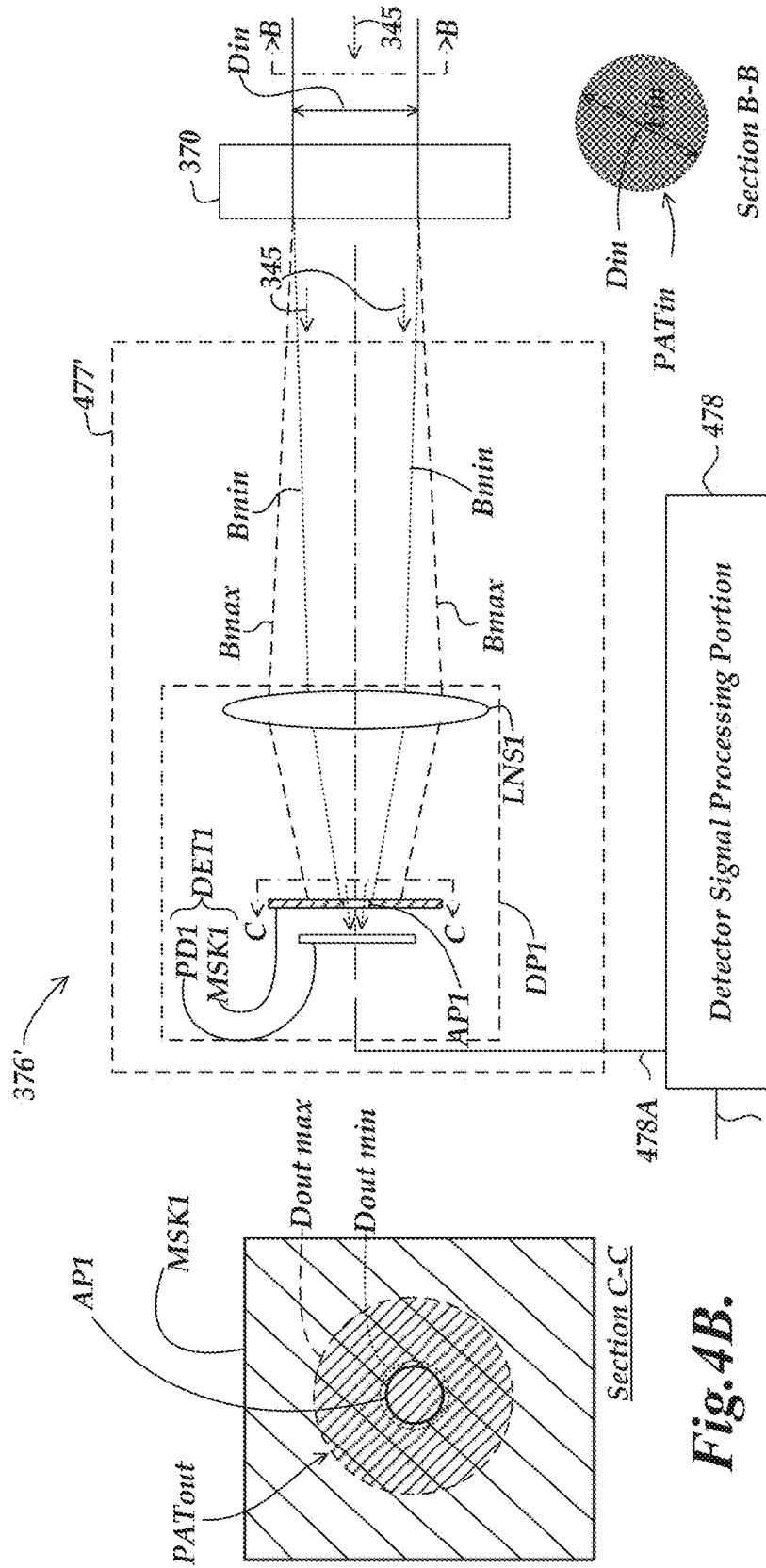

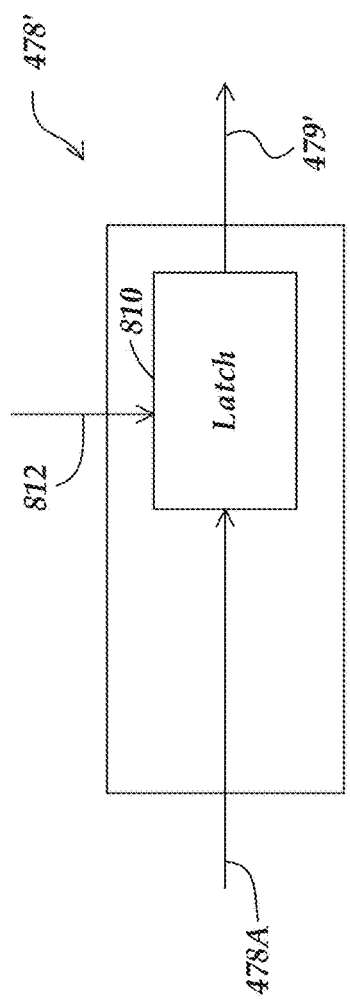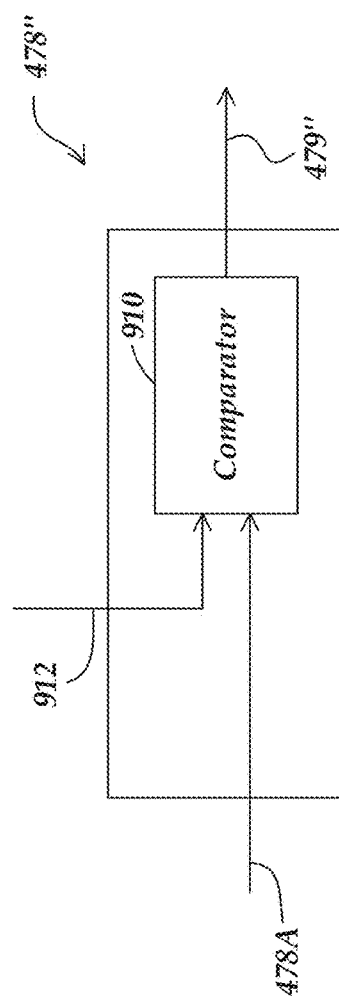
Fig. 8
Fig. 9

VARIABLE FOCAL LENGTH LENS SYSTEM WITH FOCUS MONITORING AND CONTROL

BACKGROUND

Technical Field

This disclosure relates to precision metrology using a variable focus lens, and to machine vision inspection systems and other systems in which a variable focal length lens may periodically modulate a focus position.

Description of the Related Art

Precision machine vision inspection systems (or "vision systems" for short) may be used for measuring and inspecting objects. Such systems may include a computer, camera, optical system, and a stage that moves to allow workpiece traversal. One exemplary system, characterized as a general-purpose "off-line" precision vision system, is the QUICK VISION® series of PC-based vision systems and QVPAK® software available from Mitutoyo America Corporation (MAC), located in Aurora, Ill. The features and operation of the QUICK VISION® series of vision systems and the QVPAK® software are generally described, for example, in the QVPAK 3D CNC Vision Measuring Machine User's Guide, published January 2003, which is hereby incorporated herein by reference in its entirety. This type of system uses a microscope-type optical system and moves the stage to provide inspection images of small or large workpieces at various magnifications.

In various applications, for high throughput it is desirable to perform high speed measurements in either stationary or non-stop moving inspection systems. With respect to Z-height measurements, which are generally based on the "best focus" height determination, the speed at which the Z-height measurements can be performed may be limited by the Z-height focus position adjustment or motion speed. However, some innovative variable focus lenses are able to change focus at a very high rate, and determining their actual focus position with high accuracy, at a rate commensurate with their rate of focus variation, has proved problematic. Improved Z-height measurement accuracy and speed is needed for various high-speed variable focus lenses used for high-speed precision inspection operations.

BRIEF SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

A variable focal length (VFL) lens system is provided including a tunable acoustic gradient (TAG) lens and an optical focus monitoring configuration for providing a focus monitoring signal that reflects the focus state of the VFL lens system with high accuracy and without significant latency. The TAG lens is operated to periodically modulate its optical power over a range of optical powers at an operating frequency. The optical focus monitoring configuration includes a monitoring light source and an optical focus signal detector portion. The monitoring light source is configured to input a focus detection light into the TAG lens during the periodic modulation. In various embodiments, the input focus detection light is configured to provide an input amount of light energy distributed in an input illumination pattern having an approximately constant size. In some embodiments, the input amount of light energy is approximately constant. At least a central portion of the input illumination pattern is transmitted through the TAG lens during the periodic modulation to provide a corresponding output illumination pattern from the TAG lens, wherein the output illumination pattern has a size and intensity that depends on the optical power of the TAG lens. The optical focus signal detector portion is positioned at an approximately constant distance from the TAG lens to receive focus detection light included in the output illumination pattern output from the TAG lens. The optical focus signal detector portion includes a filtering configuration and a focus photodetector that provides a focus output signal that varies in relation to the total light energy that the focus photodetector receives, wherein the filtering configuration receives the output illumination pattern and limits the amount of included focus detection light that reaches the focus photodetector. A focus monitoring signal is provided based on the focus output signal provided by the focus photodetector.

BRIEF DESCRIPTION OF THE DRAWINGS

FIGS. 4A and 4B are diagrams of an optical focus monitoring portion including a first exemplary implementation of an input illumination pattern;

FIG. 8 is a block diagram of a first exemplary implementation of a detector signal processing portion;

FIG. 9 is a block diagram of a second exemplary implementation of a detector signal processing portion.

DETAILED DESCRIPTION

Figure 1:
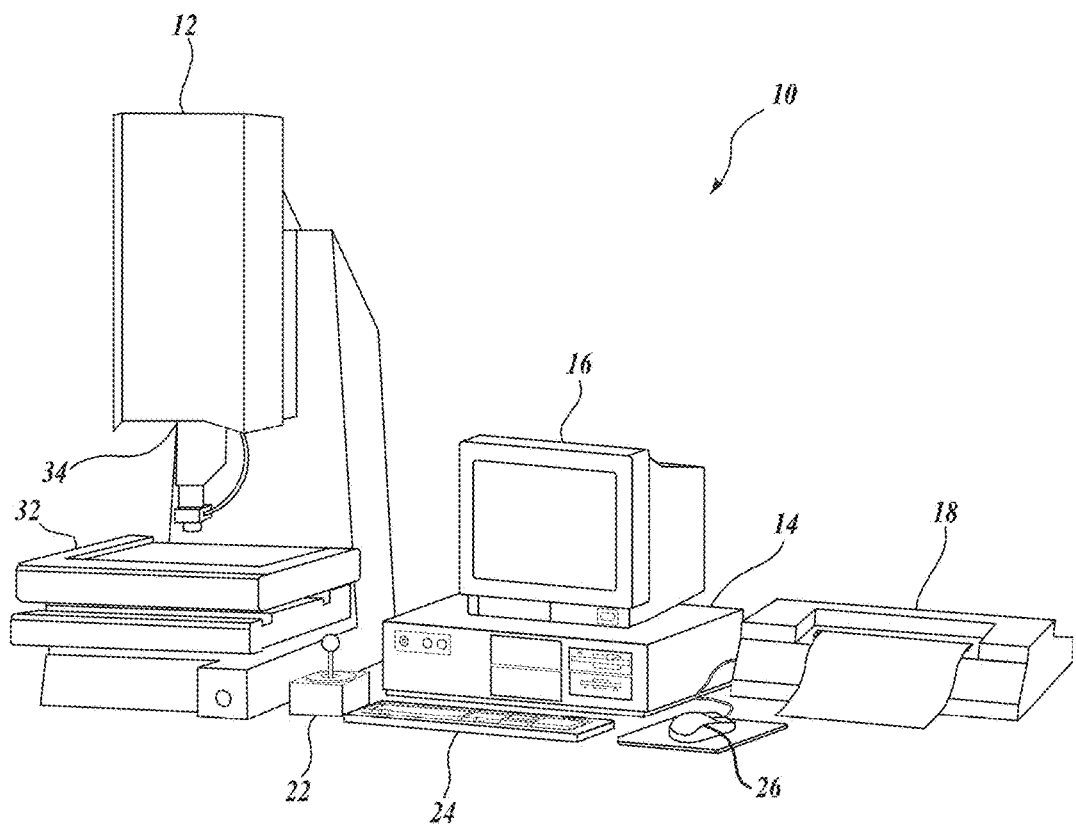
FIG. 1 is a diagram showing various typical components of a general-purpose precision machine vision inspection system.

FIG. 1 is a block diagram of one exemplary machine vision inspection system 10 usable in accordance with principles disclosed herein. The vision system 10 includes a vision measuring machine 12 operably connected to exchange data and control signals with a controlling computer system 14, a monitor or display 16, a printer 18, a joystick 22, a keyboard 24, and a mouse 26. The monitor or display 16 may display a user interface for controlling and/or programming the vision system 10. A touchscreen tablet or the like may be substituted for or augment any or all of these components.

More generally, the controlling computer system 14 may comprise or consist of any computing system or device, and/or distributed computing environment, and may include one or more processors that execute software to perform the functions described herein. Processors include programmable general- or special-purpose microprocessors, controllers, application-specific integrated circuits (ASICs), programmable logic devices (PLDs), or a combination thereof. Software may be stored in random-access memory (RAM), read-only memory (ROM), flash memory, or the like, or a combination thereof. Software may also be stored in optical-based disks, flash memory devices, or any other type of non-volatile storage medium for storing data. Software may include one or more program modules that include routines, programs, objects, components, data structures, and so on that perform particular tasks or implement particular abstract data types. The functionality of the program modules may be combined or distributed across multiple computing systems or devices and accessed via service calls, either in a wired or wireless configuration.

The vision measuring machine 12 includes a moveable workpiece stage 32 and an optical imaging system 34 that may include a zoom lens or interchangeable lenses. The zoom lens or interchangeable lenses generally provide various magnifications (e.g., 0.5× to 100×). Similar vision systems are described in commonly assigned U.S. Pat. Nos. 7,324,682; 7,454,053; 8,111,905; and 8,111,938, each of which is hereby incorporated herein by reference in its entirety.

Figure 2:
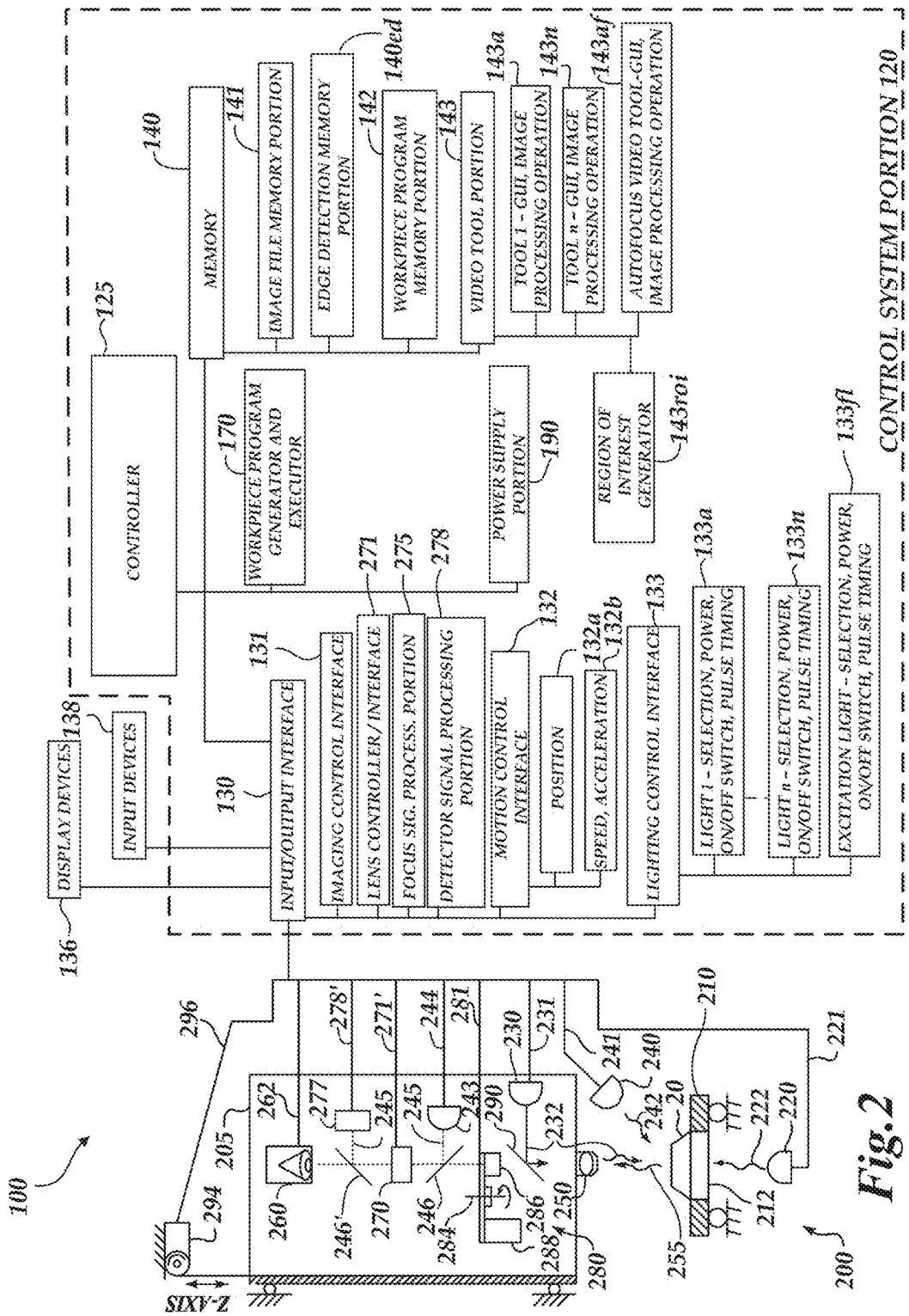
FIG. 2 is a block diagram of a control system portion and a vision components portion of a vision system similar to that of FIG. 1 and including features disclosed herein.

FIG. 2 is a block diagram of a control system portion 120 and a vision components portion 200 of a vision system 100 similar to the vision system of FIG. 1, including features as described herein. The control system portion 120 is utilized to control the vision components portion 200. The vision components portion 200 includes an optical assembly portion 205, light sources 220, 230, 240 and 243, and a workpiece stage 210 that may have a central transparent portion 212. The workpiece stage 210 is controllably movable along x- and y-axes that lie in a plane that is generally parallel to the surface of the stage where a workpiece 20 may be positioned.

The optical assembly portion 205 may include camera/detector 260 (e.g., a camera portion, and/or optionally a confocal optical focus detector, or the like), a variable focal length (VFL) lens 270, a detector configuration 277, and may also include an interchangeable objective lens 250 and a turret lens assembly 280 having lenses 286 and 288. Alternatively to the turret lens assembly, a fixed or manually interchangeable magnification-altering lens, or a zoom lens configuration, or the like, may be included.

In various implementations, the optical assembly portion 205 is controllably movable along a z-axis that is generally orthogonal to the x- and y-axes by using a controllable motor 294 that drives an actuator to move the optical assembly portion 205 along the z-axis to change the focus of an image. The controllable motor 294 is connected to an input/output interface 130 via a signal line 296. As will be described in more detail below, the VFL lens 270 may also be operated to periodically modulate a focus position. A workpiece 20, or plurality of workpieces 20, to be imaged is/are on the workpiece stage 210 which moves (e.g., in the x- and y-axes directions) relative to the optical assembly portion 205, such that the imaged area moves between locations on the workpiece(s) 20.

One or more of a stage light 220, a coaxial light 230, and a surface light 240 (e.g., a ring light), connected to the control system portion 120 through signal lines or busses 221, 231 and 241, may emit source light 222, 232, and/or 242, respectively, to illuminate the workpiece or workpieces 20, according to known principles. In FIG. 2, the source light 232 is reflected by a reflecting surface 290 to illuminate the workpiece 20. The source light is reflected or transmitted as workpiece light 255, (e.g., as used for imaging) which passes through the interchangeable objective lens 250, the turret lens assembly 280 and the VFL lens 270 to the camera/detector 260. In various implementations, the camera/detector 260 may output image data and/or other signals on a signal line or bus 262 to the control system portion 120. The control system portion 120 may rotate the turret lens assembly 280 about an axis 284 to select a turret lens magnification as controlled through a signal line or bus 281. As will be described in more detail below, in various implementations the light source 230 (or other light source) may be a controllable strobe light source that is operably connected to and controlled (e.g., through the signal line or bus 231) by a strobe controller (e.g., in the controller 125 and/or lighting control interface 133, etc.) A focus monitoring signal may be input to the strobe controller and the strobe controller may control a strobe timing of the controllable strobe light source at least in part based on the focus monitoring signal.

As will be described in more detail below with respect to FIGS. 3 and 4, a light source 243 may emit a focus detection light 245 (e.g., of a desired wavelength that does not interfere with imaging). The focus detection light 245 may be reflected by a reflecting surface 246 to pass through the VFL lens 270 and further reflected by a reflecting surface 246' toward a detector configuration 277. The detector configuration 277 may input the focus detection light 245 and output signal data (e.g., including a focus output signal and/or a focus monitoring signal, etc.) on a signal line or bus 278' to a detector signal processing portion 278 of the control system portion 120. The light source 243 may be connected to the control system portion 120 through a signal line or bus 244.

As shown in FIG. 2, in various exemplary implementations, the control system portion 120 includes a controller 125, the input/output interface 130, a memory 140, a workpiece program generator and executor 170, and a power supply portion 190. Each of these components, and additional components described below, may be interconnected by direct connections or by one or more data/control busses and/or application programming interfaces. The input/output interface 130 includes an imaging control interface 131, a motion control interface 132, and a lighting control interface 133. The motion control interface 132 may include a position control element 132a, and a speed/acceleration control element 132b, although such elements may be merged and/or indistinguishable. The lighting control interface 133 may include lighting control elements 133a, 133n, and 133fl that control, for example, the selection, power, on/off switch, and strobe pulse timing, if applicable, for the various corresponding light sources of the vision system 100.

In accordance with the principles disclosed herein, the input/output interface 130 may further include a lens controller/interface 271, a focus signal processing portion 275 and a detector signal processing portion 278, as will be described in more detail below with respect to FIGS. 3-6. Briefly, in one implementation, the lens controller/interface 271 may include a lens controller including a lens focus operating circuit and/or routine, or the like. The lens controller/interface 271 may be configured or controlled by a user and/or an operating program, and may utilize the signal line 271' to control the VFL lens 270 to periodically modulate its optical power (e.g., sinusoidally) and thereby periodically modulate a focus position of the imaging system over a plurality of focus positions along a Z-height direction at a determined operating frequency. The periodically modulated VFL lens optical power defines a periodic focus modulation. As will be described in more detail below with respect to FIG. 8, in one implementation the detector signal processing portion 278 may include a latching circuit wherein a strobe timing (e.g., for the light source 230) triggers latching of a corresponding focus monitoring signal value that is indicative of a Z-height at a corresponding image exposure timing determined by the strobe timing. As will be described in more detail below with respect to FIG. 9, in one implementation the detector signal processing portion 278 may include a comparator circuit that inputs a focus monitoring signal and a reference signal related to a Z-height in order to trigger a controllable strobe light source (e.g., the light source 230) at a Z-height that the reference signal is related to. In various implementations, the focus signal processing portion 275 may also or alternatively provide a focus position indicating signal and/or determine a focus monitoring signal value corresponding to when signal data from the camera/detector 260 (e.g., including a camera portion, a confocal optical detector, etc.) indicates that an imaged workpiece surface region is at a focus position.

In various implementations, the imaging control interface 131 and/or lens controller/interface 271 may further include an extended depth of field mode, as described in more detail in copending and commonly assigned U.S. Patent Publication No. 2015/0145980, which is hereby incorporated herein by reference in its entirety. Other systems and methods including VFL lenses are described in copending and commonly assigned U.S. patent application Ser. No. 14/795,409, entitled "Adaptable Operating Frequency of a Variable Focal Length Lens in an Adjustable Magnification Optical System", filed on Jul. 9, 2015, U.S. patent application Ser. No. 14/841,051, entitled "Multi-Level Image Focus Using a Tunable Lens in a Machine Vision Inspection System", filed on Aug. 31, 2015, and in copending and commonly assigned U.S. patent application Ser. No. 14/854,624, entitled "Chromatic Aberration Correction in Imaging System Including Variable Focal Length Lens", filed on Sep. 15, 2015, each of which is hereby incorporated herein by reference in its entirety.

The memory 140 may include an image file memory portion 141, an edge-detection memory portion 140ed, a workpiece inspection program memory portion 142, and a video tool portion 143. The video tool portion 143 includes video tool portion 143a and other video tool portions (e.g., 143n) that determine the GUI, image-processing operation, etc., for each of the corresponding video tools, and a region of interest (ROI) generator 143roi that supports operations in various video tools. An autofocus video tool 143af may determine the GUI, image-processing operation, etc., for certain focus height measurement operations. The autofocus video tool 143af may additionally include a high-speed focus height tool, as described in more detail in copending and commonly assigned U.S. Patent Publication No. 2014/0368726, which is hereby incorporated herein by reference in its entirety. In various implementations, the optical focus monitoring that is described herein (e.g., including utilization of the detector configuration 277, the detector signal processing portion 278, and/or other related elements) may be utilized in conjunction with, or otherwise included in, one or more of the video tools.

In the context of this disclosure, and as is known by one of ordinary skill in the art, the term "video tool" generally refers to automatic or programmed operations that a machine vision user can implement through a relatively simple user interface, without creating the step-by-step sequence of operations included in the video tool. For example, a video tool may include a complex pre-programmed set of image-processing operations that are applied and customized in a particular instance by adjusting a few governing variables or parameters. In addition to the underlying operations and computations, the video tool comprises the user interface that allows the user to adjust those parameters for a particular instance of the video tool. The user interface features are sometimes referred to as the video tool with the underlying operations being included implicitly.

The signal line 262 from the camera/detector 260, the signal line 271' from the VFL lens 270, the signal line 278' from the detector configuration 277 and the signal line 296 from the controllable motor 294 are connected to the input/output interface 130. In addition to carrying image data, the signal line 262 may carry a signal from the controller 125 that initiates certain processes (e.g., image acquisition, confocal brightness measurement, etc.)

User interface display devices 136 (e.g., the display 16 of FIG. 1) and input devices 138 (e.g., the joystick 22, keyboard 24, and mouse 26 of FIG. 1) may also be connected to the input/output interface 130. The display devices 136 may display user interface features associated with the lens controller/interface 271, the focus signal processing portion 275, the detector signal processing portion 278, etc., in some embodiments.

Figure 3:
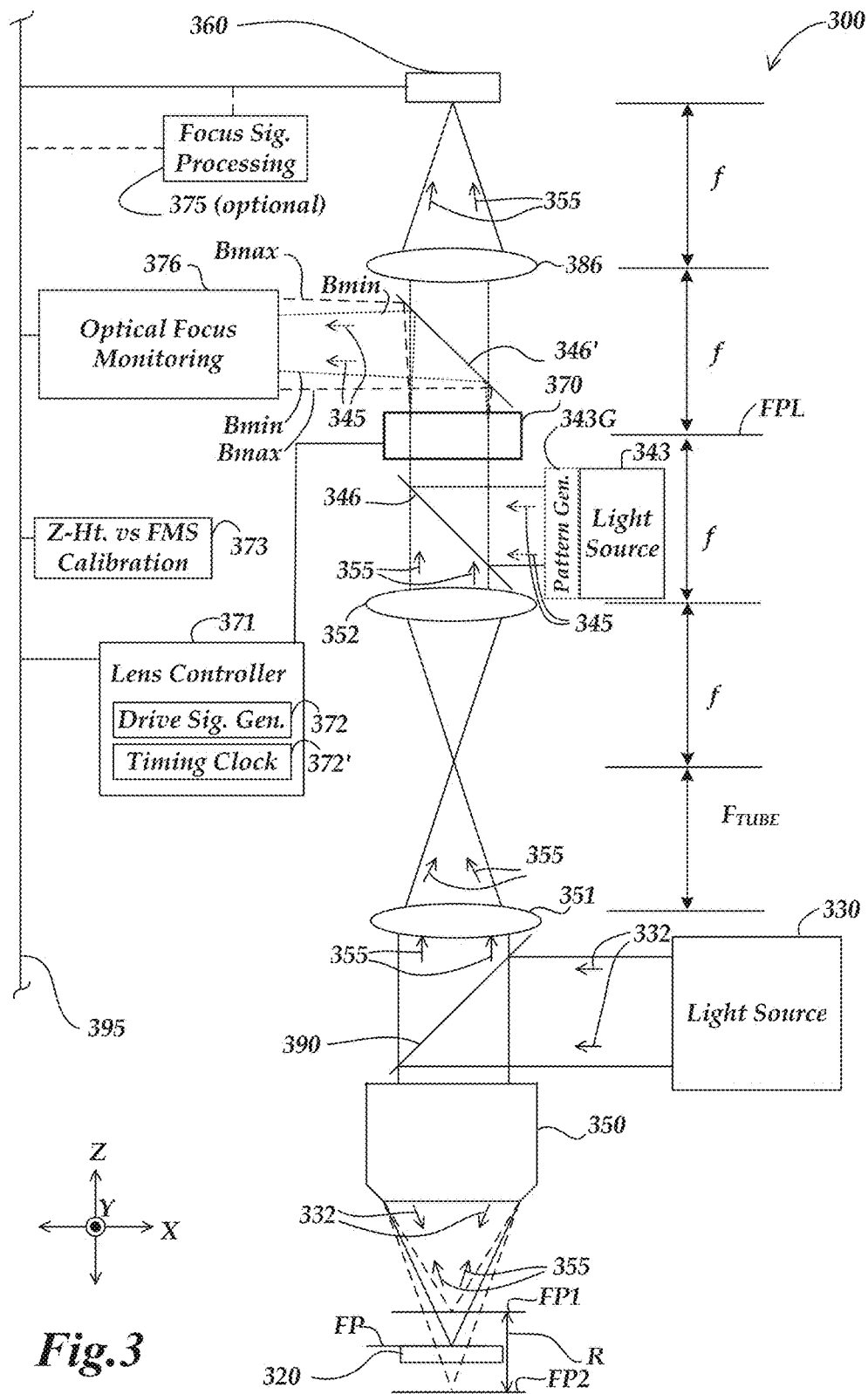
FIG. 3 is a schematic diagram of a variable focal length lens system including an optical focus monitoring portion that may be operated according to principles disclosed herein.

FIG. 3 is a schematic diagram of a VFL lens system 300 that may be adapted to a vision system and operated according to the principles disclosed herein. It will be appreciated that certain numbered components 3XX of FIG. 3 may correspond to and/or have similar operations as similarly numbered components 2XX of FIG. 2, except as otherwise described below. As shown in FIG. 3, the VFL lens system 300 includes light sources 330 and 343, an objective lens 350, a tube lens 351, a relay lens 352, a VFL lens 370, a relay lens 386, a lens controller 371, a camera/detector 360, an optical focus monitoring portion 376, and a focus monitoring signal (FMS) calibration portion 373. In various implementations, the various components may be interconnected by direct connections or one or more data/control busses (e.g., a system signal and control bus 395) and/or application programming interfaces.

In operation, in the implementation shown in FIG. 3, the light source 330 may be a "coaxial" or other light source configured to emit the source light 332 (e.g., with strobed or continuous illumination) along a path including a partial mirror 390 and through the objective lens 350 to a surface of a workpiece 320, wherein the objective lens 350 receives the workpiece light 355 that is focused at a focus position FP proximate to the workpiece 320, and outputs the workpiece light 355 to the tube lens 351. The tube lens 351 receives the workpiece light 355 and outputs it to the relay lens 352. In other implementations, analogous light sources may illuminate the field of view in a non-coaxial manner, for example a ring light source may illuminate the field of view. In various implementations, the objective lens 350 may be an interchangeable objective lens and the tube lens 351 may be included as part of a turret lens assembly (e.g., similar to the interchangeable objective lens 250 and the turret lens assembly 280 of FIG. 2). In various implementations, any of the other lenses referenced herein may be formed from or operate in conjunction with individual lenses, compound lenses, etc.

The relay lens 352 receives the workpiece light 355 and outputs it to the VFL lens 370. The VFL lens 370 receives the workpiece light 355 and outputs it to the relay lens 386. The relay lens 386 receives the workpiece light 355 and outputs it to the camera/detector 360. In various implementations, the camera/detector 360 may capture an image of the workpiece 320 during an image exposure period, and may provide the image data to a control system portion. In various implementations, the camera/detector 360 may also or alternatively include a confocal optical detector, or the like.

In various implementations, the optional focus signal processing portion 375 may input data from the camera/detector 360 and may provide data or signals that are utilized to determine when an imaged surface region (e.g., of the workpiece 320) is at a focus position. For example, in an implementation where the camera/detector 360 includes a camera, one or more images acquired by the camera (e.g., an image stack), may be analyzed using a known "maximum contrast" analysis to determine when an imaged surface region of the workpiece 320 is at a focus position. Exemplary techniques for such an analysis are taught in U.S. Pat. Nos. 6,542,180 and 9,060,117, each of which is commonly assigned and hereby incorporated herein by reference in its entirety. In an implementation where the camera/detector 360 includes a confocal optical detector, at least some of the signal data may correspond to a sensed confocal brightness. In such an implementation, the optional focus signal processing portion 375 may be utilized during the periodic modulation of the optical power of the VFL lens 370 to determine when a maximum confocal brightness occurs, as corresponding to a focus position of the workpiece 320.

The VFL lens 370 is electronically controllable to vary the focus position FP of the imaging system (e.g., during or between one or more image exposures, etc.). The focus position FP may be moved within a range R bound by a focus position FP1 and a focus position FP2. It will be appreciated that in various implementations, the range R may be selected by a user or may result from design parameters or may otherwise be automatically determined. In general, with respect to the example of FIG. 3, it will be appreciated that certain of the illustrated dimensions may not be to scale. For example, the VFL lens 370 may have different proportional dimensions than those illustrated (e.g., may be less wide and up to 50 mm long or longer for certain applications in order to provide a desired amount of lensing power, etc.).

In various implementations, a vision system may comprise a control system (e.g., the control system portion 120 of FIG. 2) that is configurable to operate in conjunction with a lens controller 371 or to otherwise control the VFL lens 370 to periodically modulate a focus position of the VFL lens system 300. In some implementations, the VFL lens 370 may rapidly adjust or modulate the focus position periodically. In various implementations, the lens controller 371 may operate to drive the VFL lens 370 (e.g., a TAG lens) at a resonant frequency in order to periodically modulate the VFL lens optical power over the range of optical powers at the operating frequency. As will be described in more detail below, a focus monitoring signal may be input to the lens controller 371 (e.g., as a feedback signal) and used to adjust the control of the VFL lens 370. In various implementations, the adjustment of the control of the VFL lens 370 may include adjusting at least one of the amplitude, frequency, or phase of the periodic modulation of the VFL lens 370.

In one example implementation, the range R over which the focus position FP may be moved may be approximately 10 mm (e.g., for a 1× objective lens 350). In various implementations, the VFL lens 370 is advantageously chosen such that it does not require any macroscopic mechanical adjustments in the imaging system and/or adjustment of the distance between the objective lens 350 and the workpiece 320 in order to change the focus position FP.

In various implementations, the VFL lens 370 may be a tunable acoustic gradient index of refraction ("TAG") lens. A tunable acoustic gradient index of refraction lens is a high-speed VFL lens that uses sound waves in a fluid medium to modulate a focus position and may periodically sweep a range of focal lengths at a frequency of several hundred kHz. Such a lens may be understood by the teachings of the article, "High-speed varifocal imaging with a tunable acoustic gradient index of refraction lens" (Optics Letters, Vol. 33, No. 18, Sep. 15, 2008), which is hereby incorporated herein by reference in its entirety. Tunable acoustic gradient index lenses and related controllable signal generators are available, for example, from TAG Optics, Inc., of Princeton, N.J. The Model TL2.B.xxx series lenses, for example, are capable of modulation up to approximately 600 KHz.

The VFL lens 370 may be driven by the lens controller 371, which may generate a signal to operate the VFL lens 370. In one embodiment, the lens controller 371 may be a commercial controllable signal generator. In some implementations, the lens controller 371 may be configured or controlled by a user and/or an operating program (e.g., through the lens controller/interface 271, as outlined previously with respect to FIG. 2). In some implementations, the lens controller 371 may control the VFL lens 370 to periodically modulate its optical power (e.g., sinusoidally) and thereby periodically modulate a focus position of the imaging system over a plurality of focus positions along a Z-height direction at a high operating frequency (e.g., as high as 400 kHz, or 600 kHz, etc.), although slower focus position modulation frequencies may be desirable in various implementations and/or applications. For example, in various implementations a periodic modulation of 300 Hz, or 3 kHz, or 70 kHz, or 250 kHz, or the like, may be used. In implementations where slower periodic focus position adjustments are used, the VFL lens 370 may comprise a controllable fluid lens, or the like. In various implementations, the periodically modulated VFL lens optical power may define a periodic focus modulation.

In various implementations, the lens controller 371 may include a drive signal generator portion 372. The drive signal generator portion 372 may operate (e.g., in conjunction with a timing clock 372') to provide a periodic drive signal to a high speed VFL such as a TAG lens. In various implementations, the periodic signal may have the same operating frequency as the periodically modulated VFL lens optical power, and in a prior art TAG lens the approximate focus height or Z-height of a TAG lens has been determined based on a concurrent state of the drive signal. However, due to the high focus variation frequency and other operating characteristics of a TAG lens, the drive signal may be slightly out of phase with the actual focus height or Z-height variation of the TAG lens, leading to Z-height measurement errors and/or the need for complex and error compensation schemes such as described in copending and commonly assigned U.S. patent application Ser. No. 15/145,682, entitled "Phase Difference Calibration In A Variable Focal Length Lens System", filed on May 3, 2016, which is hereby incorporated herein by reference in its entirety. The principles disclosed herein may be used to overcome deficiencies in the prior art, and/or eliminate the need for complex error compensation schemes, in order to provide precision Z-height measurements for high speed VFL's such as a TAG lens.

According to principles disclosed herein, a focus monitoring signal may be determined which is directly indicative of the periodic focus modulation, approximately in real time, as will be described in more detail below. In various implementations, the Z-height versus focus monitoring signal calibration portion 373 may provide a first Z-height versus focus monitoring signal value characterization that relates respective Z-heights to respective focus monitoring signal values. Generally speaking, the Z-height versus focus monitoring signal calibration portion 373 comprises recorded calibration data. As such, its representation in FIG. 3 as a separate element is only schematic, and not limiting. The associated recorded calibration data could be merged with and/or indistinguishable from the lens controller 371, or the optical focus monitoring portion 376, or a host computer system connected to the system signal and control bus 395, in various embodiments.

As will be described below with respect to FIG. 4, the optical focus monitoring portion 376 may input focus detection light 345 that has passed through the VFL lens 370 and may produce a focus output signal (e.g., a focus output signal from a photodetector). In various implementations, a focus monitoring signal may be provided based on the focus output signal. For example, in one implementation, the focus output signal may be provided directly as the focus monitoring signal. As another example, in an alternative implementation, the focus monitoring signal may be produced based on further signal processing of the focus output signal.

As will be described in more detail below, in various implementations the VFL lens system 300 may further include a pattern generator 343G that in combination with the light source 343 generates an input illumination pattern PATin that is input into the VFL lens 370 (e.g., a TAG lens) and that results in an output illumination pattern PATout from the VFL lens 370. In various implementations, an optical path including the VFL lens 370 may further include a first beamsplitter 346 and a second beamsplitter 346'. The first beamsplitter 346 is located between the objective lens 350 and the VFL lens 370 and receives focus detection light 345 from the monitoring light source 343 and directs at least some of the focus detection light 345 to pass through the VFL lens 370. The second beamsplitter 346' is located between the VFL lens 370 and the camera/detector 360 and receives the output illumination pattern PATout from the VFL lens 370 and directs the output illumination pattern PATout toward the optical focus monitoring portion 376 including an optical focus signal detector portion (e.g., as will be described in more detail below with respect to FIGS. 4-6).

In the specific configuration of FIG. 3, the light source 343 in combination with the pattern generator 343G produces focus detection light 345 in the form of a collimated beam (e.g., in the form of the input illumination pattern PATin), at least some of which is received by the beamsplitter 346 and is directed to pass through the VFL lens 370. The beamsplitter 346' receives at least some of the focus detection light 345 that has passed through the VFL lens 370 (e.g., in the form of the output illumination pattern PATout) and directs the focus detection light toward the optical focus monitoring portion 376. Due to the positioning and modulating optical power of the VFL lens 370, the focus detection light 345 may be output from the VFL lens with divergence/convergence for which the outer beam dimensions are correspondingly modulated and vary between maximum outer beam paths Bmax and minimum outer beam paths Bmin (e.g., which may cause certain dimensions of the output illumination pattern PATout to correspondingly modulate/vary, as will be described in more detail below with respect to FIGS. 4A, 4B and 5A-5D).

In one implementation, the beamsplitters 346 and 346' may be dichroic beamsplitters and the focus detection light 345 from the light source 343 may be of a different wavelength than the source light 332 from the light source 330. In various implementations, the monitoring light source 343 may produce the focus detection light 345 consisting of a first set of wavelengths and the imaging light source 330 may produce the source light 332 consisting of a second set of wavelengths that excludes the first set of wavelengths. The dichroic beamsplitters 346 and 346' may each reflect the first set of wavelengths and transmit the second set of wavelengths. As an example, in one specific implementation, the light source 343 may be operated in a continuous mode and may provide collimated focus detection light 345 with a wavelength of approximately $\lambda=735$ nm, for which one or both of the dichroic beamsplitters 346 and 346' may have characteristics such as R>720 nm and T<700 nm (e.g., so as to reflect the desired focus detection light 345 from the light source 343 while allowing workpiece light 355 that results from the source light 332 from the light source 330 to pass through as transmitted light to the camera/detector 360, etc.).

As described above, the source light 332 from the light source 330 may be directed toward an imaged surface region (e.g., of the workpiece 320) to produce the workpiece light 355 (e.g., that is utilized to produce an image of the imaged surface region and/or to determine when the imaged surface region is in focus), and for which the source light 332 may have a different wavelength than the focus detection light 345 (e.g., the source light 332 being $\lambda<700$ nm while the focus detection light 345 is $\lambda>720$ nm, etc.). In various implementations, utilization of a 735 nm LED for the light source 343 to produce the focus detection light 345 may have certain advantages (e.g., having a good match to silicon responsivity and having little or no coherence/speckle, etc.). As another example where more power is needed, a 785/805 nm diode laser may be utilized as operated below threshold, etc.

In various implementations, an imaging configuration may be designated as including at least the objective lens 350, the VFL lens 370, and the camera/detector 360. As noted above, the objective lens 350 inputs workpiece light 355 from an imaged surface region of the workpiece 320 in the field of view (FOV) of the imaging configuration and transmits the workpiece light 355 through the VFL lens 370, and the camera/detector 360 receives the workpiece light from the VFL lens 370 and provides an image focused at an imaging system focal plane having at least one of a focus distance or Z-height relative to the imaging configuration. In various implementations, at least one of the focus distance or Z-height of the imaging system focal plane is controlled by the VFL lens optical power. In such implementations, an instantaneous value of focus monitoring signal that is produced by the optical focus monitoring portion 376 may be indicative of at least one of the instantaneous focus distance or Z-height of the imaging system focal plane. In various implementations, the focus monitoring signal and/or focus output signal may comprise a time varying signal that is indicative of the focus state of the VFL lens 370 throughout the modulation period with high accuracy and the time varying signal may be provided without significant latency compared to the focus state. In one specific example configuration, the periodic modulation may correspond to a frequency of at least 50 kHz, and the time varying signal may be provided with a latency compared to the focus state of not more than 100 nanoseconds. In some embodiments, even smaller latency may be attained, for example not more than 50 nanoseconds, or 25 nanoseconds, or less. Suitable ultrafast photodetectors and associated amplification circuits are known in the art and commercially available, for example, from Hamamatsu Corporation, San Jose, Calif., and/or Newport Corporation, Santa Clara, Calif. Such photodetectors may have a rise time on the order of 40 picoseconds, for example. The associated latencies or signal lag may thus correspond to an insignificant focus measurement error or Z-height error in an imaging system using a periodically modulated high speed VFL lens such as a TAG lens, in that the focus change during the small latency period may be a small portion of the depth of field of the imaging system including the VFL lens. In various implementations, any residual latency may further be compensated for or otherwise accounted for by circuitry (e.g., included in the detector signal processing portion 478 of FIGS. 8 and 9) and/or other components of the VFL lens system 300. It will be appreciated that according to principles disclosed herein, the near real-time monitoring of the actual optical power of the VFL lens allows Z-height measurements and/or other operations of the VFL lens system to be accurately performed despite various instabilities (e.g., lens or circuit temperature sensitivity) that adversely affected prior art methods.

In various implementations, the focus monitoring signal may be utilized for various purposes relative to the operations of the VFL lens system 300. For example, the focus monitoring signal may be input to a controller which may utilize the focus monitoring signal (e.g., as a feedback signal) to adjust the control of the VFL lens 370. As another example, a VFL lens system may generally be configured to control the image exposure using an image exposure timing that determines the corresponding imaging system focal plane. The VFL lens system may be configured to control at least one of a timing of a controllable strobe light source that is included in VFL lens system or a timing of a controllable image integration period of the camera portion, to provide the image exposure timing. In some embodiments, a latching circuit may be configured to latch a focus monitoring signal value at a time corresponding to the image exposure timing, wherein the latched focus monitoring signal value is indicative of the focus distance or Z-height for the corresponding image exposure. In some embodiments, a comparator circuit may be configured to input the focus monitoring signal and input a reference signal related to a desired imaging focus distance or Z-height, and output a trigger signal that controls the image exposure timing to occur when the focus monitoring signal corresponds to the reference signal. In some embodiments, the focus monitoring signal may be input to the controller for controlling the image exposure timing, or the focus monitoring portion 376 may include circuitry that is utilized to control a strobe timing of the controllable strobe light source and/or the image integration period of the camera portion, at least in part based on the focus monitoring signal. Exemplary specific implementations are described in more detail below with respect to FIG. 8 and FIG. 9.

In the example of FIG. 3, the relay lenses 352 and 386 and the VFL lens 370 are designated as being included in a 4f optical configuration, while the relay lens 352 and the tube lens 351 are designated as being included in a Keplerian telescope configuration, and the tube lens 351 and the objective lens 350 are designated as being included in a microscope configuration. All of the illustrated configurations will be understood to be exemplary only, and not limiting with respect to the present disclosure. In various implementations, the illustrated 4f optical configuration permits placing the VFL lens 370 (e.g., which may be a low numerical aperture (NA) device, such as a TAG lens), at the fourier plane FPL of the objective lens 350. This configuration may maintain the telecentricity at the workpiece 320 and may minimize scale change and image distortion (e.g., including providing constant magnification for each Z-height of the workpiece 320 and/or focus position FP). The Keplerian telescope configuration (e.g., including the tube lens 351 and the relay lens 352) may be included between the microscope configuration and the 4f optical configuration, and may be configured to provide a desired size of the projection of the objective lens clear aperture at the location of the VFL lens, so as to minimize image aberrations, etc.

FIGS. 4A and 4B are diagrams of an optical focus monitoring portion 376' including a first exemplary implementation of an input illumination pattern PATin. The optical focus monitoring portion 376' may be understood to be one implementation of the optical focus monitoring portion 376 shown in FIG. 3. The beamsplitter 346' shown in FIG. 3 is omitted in the schematically represented optical path shown in FIG. 4A, for simplicity. In the example of FIG. 4A, the optical focus monitoring portion 376' includes a detector configuration 477' and a detector signal processing portion 478 (e.g., which may correspond to or otherwise be similar to the detector configuration 277 and the detector signal processing portion 278 of FIG. 2). The detector configuration 477' includes a first optical focus signal detector portion DP1 which includes a first monitoring lens LNS1 and a first optical detector DET1. The first optical detector DET1 includes a first focus photodetector PD1 and a first filtering configuration MSK1 (e.g., a mask). As will be described in more detail below with respect to FIG. 6, in an alternative configuration, a second detector portion DP2 may be included as part of a detector configuration.

As described above with respect to FIG. 3, the monitoring light source 343 is configured to input the focus detection light 345 into the VFL lens 370 during the periodic modulation. In the examples of FIGS. 4A-6, the VFL lens 370 is designated as being a TAG lens. As illustrated in FIG. 4A, in some embodiments, the input focus detection light 345 is configured to provide an input amount of light energy Ein distributed in the input illumination pattern PATin (e.g., as generated by the pattern generator 343G of FIG. 3) having an approximately constant size (e.g., as indicated by a constant diameter Din, etc.). In some embodiments, the input amount of light energy is approximately constant. The focus detection light 345 is at least approximately collimated in the input illumination pattern PATin.

In various implementations, the input focus detection light 345 in the form of the input illumination pattern PATin may comprise a static beam of light. In one such implementation, the static beam of light may comprise a solid cross-section of light that overfills a limiting aperture included in the TAG lens 370, and the limiting aperture in the TAG lens 370 may define an approximately constant size (e.g., including the diameter Din, etc.) of the input illumination pattern PATin. In another such implementation, the static beam of light may be configured in the input illumination pattern PATin having a constant size that is small enough that the complete input illumination pattern PATin passes through the TAG lens 370 to form an output illumination pattern PATout.

In various implementations, at least a central portion of the input illumination pattern PATin is transmitted through the TAG lens 370 during the periodic modulation to provide the corresponding output illumination pattern PATout from the TAG lens 370, wherein the output illumination pattern PATout has a size and intensity that depends on the optical power of the TAG lens 370. For example, as illustrated in FIG. 4B, the output illumination pattern PATout may have a size that modulates/varies between a maximum diameter Dout_max and a minimum diameter Dout_min. This variation is due at least in part due to the fact that, as a result of the positioning and modulating optical power of the TAG lens 370, the focus detection light 345 is output from the TAG lens with divergence/convergence for which the outer beam dimensions are correspondingly modulated and vary between maximum outer beam path limits Bmax and minimum outer beam path limits Bmin.

The optical focus signal detector portion DP1 is positioned at an approximately constant distance from the TAG lens 370 to receive the focus detection light 345 included in the output illumination pattern PATout that is output from the TAG lens 370. The first monitoring lens LNS1 focuses focus detection light toward the first filtering configuration MSK1 and the first focus photodetector PD1. In various implementations, the first filtering configuration MSK1 and/or the first focus photodetector PD1 may be positioned at or near the best-focus of the first monitoring lens LNS1. In various implementations, the first monitoring lens LNS1 inputs the output illumination pattern PATout and transmits it to the filtering configuration MSK1 with a reduced size. The focus photodetector PD1 provides a focus output signal 478A (e.g., corresponding to the signal line/bus 278' of FIG. 2) that varies in relation to the total light energy that the focus photodetector PD1 receives, wherein the filtering configuration MSK1 receives the output illumination pattern PATout and limits the amount of included focus detection light 345 that reaches the focus photodetector PD1.

In the example of FIGS. 4A and 4B, the input illumination pattern PATin comprises a solid pattern and is configured such that the corresponding output illumination pattern PATout that is output from the TAG lens comprises a solid pattern. The filtering configuration MSK1 comprises a spatial filtering aperture AP1 that is defined by the limits of the focus photodetector PD1 (e.g., so that the amount of the solid pattern PATout reaching the focus photodetector PD1 is of a specified size relative to the operable area of the focus photodetector PD1), and the solid pattern PATout overfills the aperture AP1 and/or focus photodetector PD1 at all times during the periodic modulation.

A focus monitoring signal is provided based on the focus output signal 478A provided by the focus photodetector PD1. In one implementation, the focus output signal 478A may correspond to and be provided directly as an amplified focus monitoring signal. In an alternative implementation, the focus output signal 478A may undergo additional signal processing and/or otherwise be modified (e.g., by known linearization and/or normalization circuit techniques, for example) and the processed/modified signal that is based on the first focus output signal 478A may be provided as a focus monitoring signal. In some implementations, as will be described in more detail below with respect to FIGS. 8 and 9, a detector signal processing portion 478 may input the first focus output signal 478A and processes it (e.g., in combination with other signals) to output an output signal 479 (e.g., as utilized to trigger a controllable strobe light source, or to determine a Z-height corresponding to when a controllable strobe light source was triggered, etc.).

In various implementations, the focus photodetector PD1 may be a high-speed photodetector that is utilized for accurately monitoring the rapidly changing optical power of the TAG lens 370 in real time. For example, in certain implementations the optical power of the VFL lens 370 may be modulated at rates as high as 50 kHz, 70 kHz, or 250 kHz, or 400 kHz, etc., for which a high-speed focus photodetector (e.g., such as previously outlined herein) may be required for accurate monitoring with minimal latency. In some implementations, the focus photodetector PD1 may be a high-speed, reverse-biased, silicon photodiode (SiPD) using a transimpedance amplifier. An example of devices and circuits that may be utilized in such configurations are described in U.S. Pat. Nos. 4,029,976; 8,907,729; and 6,064,507, for example, each of which is hereby incorporated by reference herein in its entirety.

Figure 5A:
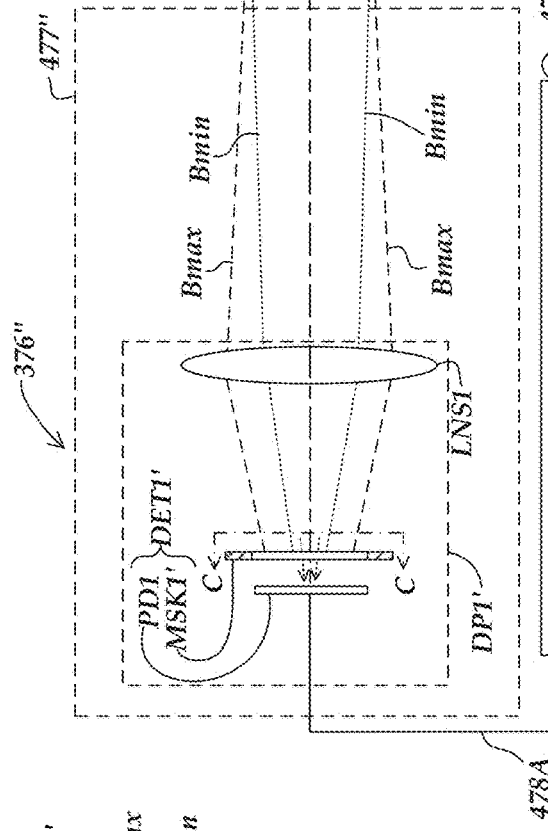
FIGS. 5A-5D are diagrams of an optical focus monitoring portion including a second exemplary implementation of an input illumination pattern and illustrating different configurations of a spatially filtering aperture or mask that may be utilized in various implementations.

FIGS. 5A-5D are diagrams of an optical focus monitoring portion 376" including a second exemplary implementation of an input illumination pattern PATin' and illustrating different configurations of spatially filtering apertures AP1'-AP1''' and corresponding filtering configurations MSK1'-MSK1''' that may be utilized in various implementations. Various elements of FIGS. 5A-5D may be similar or identical to those of FIGS. 4A and 4B, as including similar or identical reference numbers, and will be understood to operate similarly, except as otherwise described below. In the example of FIG. 5A, the optical focus monitoring portion 376" includes a detector configuration 477" and the detector signal processing portion 478. The detector configuration 477" includes a first optical focus signal detector portion DP1' which includes a first monitoring lens LNS1 and a first optical detector DET1'. The first optical detector DET1' includes a first focus photodetector PD1 and a first filtering configuration MSK1' (e.g., a mask).

Figure 5B:
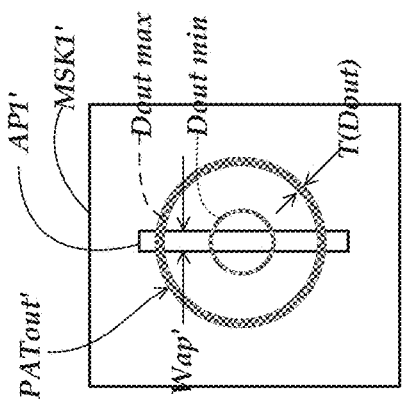
Figure 5C:
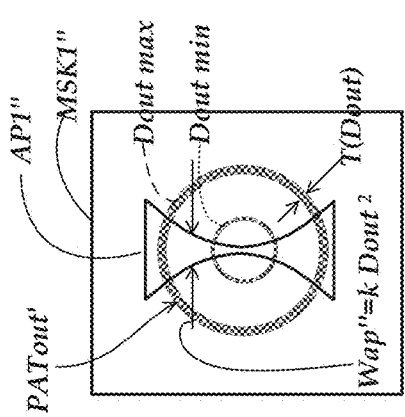
Figure 5D:
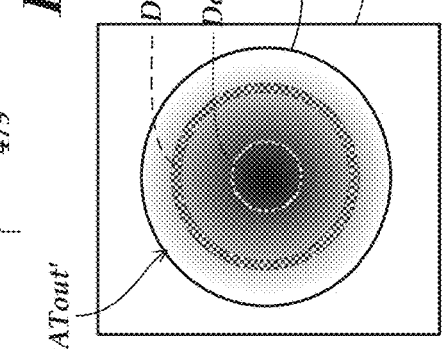

One difference for the configuration of FIG. 5A as compared to the configuration of FIG. 4A, is that the input illumination pattern PATin' is an annular pattern that is configured such that the corresponding output illumination pattern PATout' also comprises an annular pattern (e.g., a circular ring pattern). As illustrated in FIGS. 5B-5D, the output illumination pattern PATout' has a size that modulates/varies between a maximum diameter Dout_max with a corresponding maximum pattern thickness T_Dout_max, and a minimum diameter Dout_min with a corresponding minimum pattern thickness T_Dout_min.

FIGS. 5B-5D illustrate different implementations of filtering configurations MSK1'-MSK1''' (e.g., masks), including different types of spatially filtering apertures AP1'-AP1''', respectively. As will be described in more detail below with respect to FIG. 7, the different filtering configurations MSK1'-MSK1''' result in different types of relationships between a focus monitoring signal and a determined Z-height (focus distance). As shown in FIGS. 5B and 5C, for each of the filtering configurations MSK1' and MSK1", the spatially filtering apertures AP1' and AP1" of the masks have different shapes. More specifically, the spatially filtering aperture AP1' has a constant width Wap', while the spatially filtering aperture AP1" is curved and has a width Wap" defined by a function $kDout^2$. Each of the masks of the filtering configurations MSK1' and MSK1" blocks a blocked portion of the output illumination pattern PATout at all times during the periodic modulation. Each of the spatially filtering apertures AP1' and AP1" also transmits a transmitted portion of the output illumination pattern PATout at all times. In addition, each of the spatially filtering apertures AP1' and AP1" is shaped such that the ratio of the transmitted portion to the blocked portion of the output illumination pattern PATout varies depending on the size of the output illumination pattern PATout. This is in contrast, for example, to a "pie-shaped" spatially filtering aperture, for which the ratio of the transmitted portion to the blocked portion would remain constant. As will be described in more detail below with respect to FIG. 7, the shape of the spatially filtering aperture AP1" (i.e., for which Wap"=kDout^2) causes the focus output signal and/or the focus monitoring signal to be proportional to the focus state of the variable focal length (VFL) lens system.

As shown in FIG. 5D, the filtering configuration MSK1''' includes a mask comprising a density filter AP1''' having a non-uniform density pattern configured to attenuate the transmission of the output illumination pattern PATout depending on the size (e.g., the diameter Dout) of the output illumination pattern PATout. In the example of FIG. 5D, the non-uniform density pattern is axisymmetric and the density varies as a function of radius within the pattern (e.g., defined as a function of Dout, such as density=kDout). The density filter AP1''' is configured to receive and transmit the entire output illumination pattern PATout to the photodetector PD1 at all times during the periodic modulation, although as filtered by the non-uniform density pattern. As will be described in more detail below with respect to FIG. 7, the non-uniform density pattern of the density filter AP1''' (e.g., with a transmission function such as density=kDout) may cause the focus output signal and/or the focus monitoring signal to be proportional to the focus state of the variable focal length (VFL) lens system.

Figure 6:
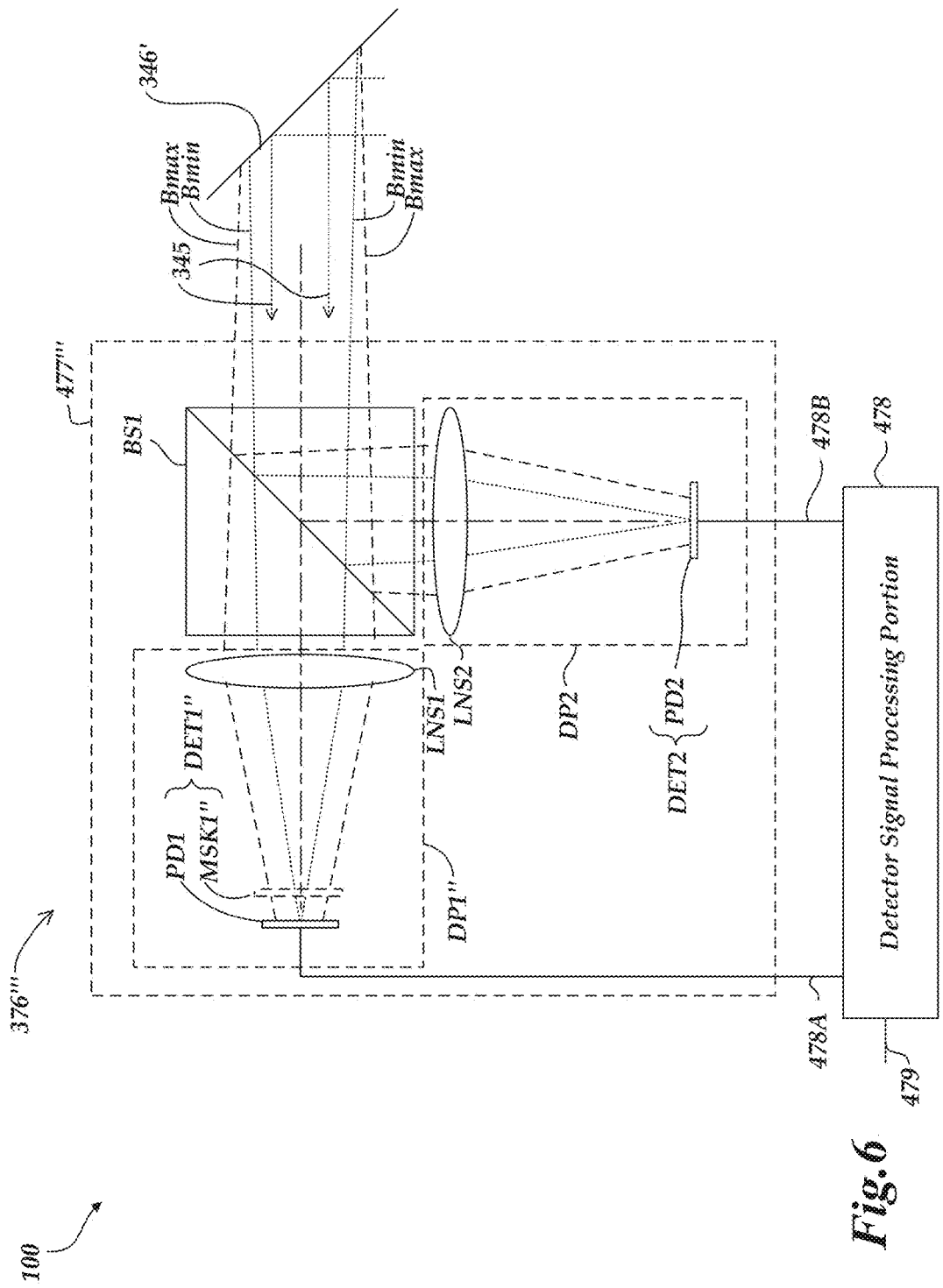
FIG. 6 is a diagram of an optical focus monitoring portion including a normalization portion.

FIG. 6 is a diagram of an optical focus monitoring portion 376''' including a normalization portion DP2. Certain elements of FIG. 6 are similar or identical to those of FIGS. 4A, 4B and 5A-5D, as including similar or identical reference numbers, and will be understood to operate similarly, except as otherwise described below. In particular, the optical focus signal detector portion DP1" may be configured similarly to any of the previously outlined embodiments of the optical focus signal detector portions DP1 or DP1'. In the example of FIG. 6, the optical focus monitoring portion 376''' includes a detector configuration 477''' and the detector signal processing portion 478. The detector configuration 477''' includes a beamsplitter BS1, the first optical focus signal detector portion DP1", and a second optical focus signal detector portion DP2 (e.g., also referenced as a normalization signal detector portion DP2). The first optical focus signal detector portion DP1" includes a first monitoring lens LNS1 and a first optical detector DET1". The first optical detector DET1" includes a first focus photodetector PD1 and a first filtering configuration MSK1" (e.g., a mask). The normalization signal detector portion DP2 includes a second monitoring lens LNS2 (e.g., also referenced as a normalization lens LNS2) and a second optical detector DET2 (e.g., also referenced as a normalization optical detector DET2), which includes a second focus photodetector PD2 (e.g., also referenced as a normalization photodetector PD2).

In operation, the beamsplitter BS1 (e.g., a non-polarizing 50/50 beamsplitter) receives focus detection light 345 as part of the output illumination pattern PATout (e.g., from the beamsplitter 346' of FIG. 3) that has passed through the TAG lens 370, and transmits at least some focus detection light as a first split output illumination pattern toward the optical focus signal detector portion DP1", which operates according to previously outlined principles. At least some focus detection light is also directed as a second split output illumination pattern toward the normalization signal detector portion DP2. The normalization signal detector portion DP2 including the normalization lens LNS2 inputs the entire second split output illumination pattern and transmits the entire second split output illumination pattern to the normalization photodetector PD2 with a reduced size, wherein the normalization photodetector PD2 provides a normalization output signal 478B (e.g., corresponding to the signal line/bus 278' of FIG. 2) that varies in relation to the total light energy it receives. In various implementations, the detector signal processing portion 478 may include, or be part of, a focus monitoring output circuit that is configured to input the focus output signal 478A and the normalization output signal 478B, and to produce a normalized focus output signal and/or a normalized focus monitoring signal, wherein variations in the focus output signal 478A due to variations in the total light energy included in the output illumination pattern PATout are compensated based on the normalization output signal 478B according to known techniques (e.g., by dividing the focus output signal 478A by the normalization output signal 478B).

Figure 7:
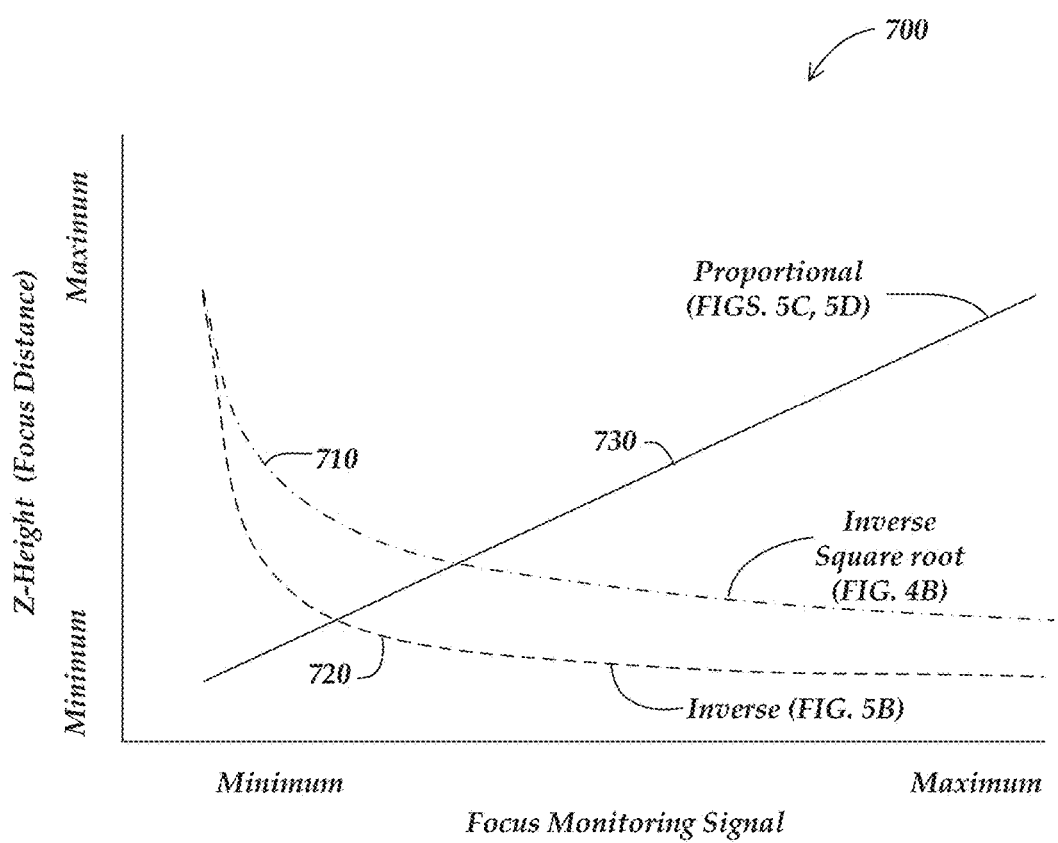
FIG. 7 is a diagram of a graph illustrating relationships between a focus monitoring signal and a Z-height (focus distance) for various optical focus monitoring portions.

FIG. 7 is a diagram of a graph 700 illustrating relationships between a focus monitoring signal (e.g., as output from a focus photodetector) and a Z-height (focus distance) for various optical focus monitoring configurations. As illustrated in FIG. 7, a curve 710 represents the output from the focus photodetector PD1 when the filtering configuration MSK1 of FIG. 4B is utilized. A curve 720 represents the output from the focus photodetector PD1 when the filtering configuration MSK1' of FIG. 5B is utilized. A curve 730 represents the output from the focus photodetector PD1 when the filtering configuration MSK1" of FIG. 5C is utilized or when the filtering configuration MSK1''' of FIG. 5D is utilized. The curves 710-730 may be better understood with reference to the following equations. In the following equations, a constant K is designated as representing a combined value of all constants that may exist in the equation, such that for each equation in which one or more constant values are present, there will only be one generic constant K illustrated.

As a first relevant equation, the intensity i(t) in the pattern at the mask plane may be represented by:

$$i(t) = Ein/A(t) \quad (Eq. 1)$$

where Ein is the total energy in the input pattern PATin, and A(t) is the total area in the output pattern at the mask plane. For the signal S(t):

$$S(t) = I(t) * Tr \quad (Eq. 2)$$

where Tr may be the transmitted area, or alternatively the transmitted area times a filtering coefficient. In the following equations, it is assumed that Zfocus is approximately proportional to Dout, such that:

$$Zfocus(t) = K(Dout(t)) \quad (Eq. 3)$$

For the solid pattern and spot configuration of FIGS. 4A and 4B:

$$A(t) = pi * (Dout(t)/2)^2 \quad (Eq. 4)$$

for which if the fixed mask aperture (Tr=constant) of FIG. 4B is utilized that is always overfilled, the signal is proportional to the intensity. That is:

$$S(t) = K*i(t) = K[Ein/pi*(Dout(t)/2)^2] \quad (Eq. 5)$$

Assuming Ein is constant (as it may be in some embodiments), and rearranging (and using K as noted above to represent any modified constant of proportionality):

$$S(t)=K/(Dout(t)/2)^2 \quad \text{(Eq. 6)}$$

which results in:

$$Zfocus(t)=K[(1/S(t)]^{1/2} \quad \text{(Eq. 7)}$$

That is, Zfocus is approximately inversely proportional to the square root of the signal S(t). In various implementations, a related calibration table may be provided, or a conversion may be performed analytically.

For the annulus pattern and filtering configuration of FIG. 5B:

$$A(t)=\text{pi}*[Dout(t)*T(Dout)] \quad \text{(Eq. 8)}$$

for which the filtering configuration MSK1' utilizes the mask aperture AP1' that has a constant width Wap' for all values of D (or Dout). In such a configuration:

$$Tr=2*Wap'*T(Dout) \quad \text{(Eq. 9)}$$

With reference to EQUATION 2, and substituting for Tr using EQUATION 9 and for i(t) using EQUATION 1:

$$S(t)=i(t)*Tr=Tr*i(t)=Tr*[Ein/A(t)]=Wap'*T(Dout)*[Ein/A(t)] \quad \text{(Eq. 10)}$$

and further substituting for A(t) using EQUATION 8:

$$S(t)=Wap'*T(Dout)Ein/[\text{pi}*Dout(t)*T(Dout)] \quad \text{(Eq. 11)}$$

Assuming Ein is constant (as it may be in some embodiments), and rearranging (and utilizing K as a modified constant of proportionality for Ein and pi, etc.):

$$S(t)=K*Wap'/Dout(t) \quad \text{(Eq. 12)}$$

In an implementation where Zfocus is approximately proportional to Dout, this results in:

$$Zfocus(t)=K\ Wap'/S(t) \quad \text{(Eq. 13)}$$

Or, since Wap' is constant in the embodiment of FIG. 5B:

$$Zfocus(t)=K/S(t) \quad \text{(Eq. 14)}$$

That is, Zfocus is approximately inversely proportional to the signal S(t), as indicated by the curve 720 of FIG. 7. With respect to the above equations, it will be appreciated that the shape of the aperture may be utilized to influence the relationship between Zfocus and the signal S(t).

Using this concept, if Wap'=K*Dout² in EQUATION 12, then the signal is proportional to Dout, and as a result Zfocus(t) is proportional to the signal S(t). One such configuration is illustrated in FIG. 5C (e.g., where the aperture AP1" flares open like a horn at increasing D such that it subtends a greater portion or angle of the output illumination pattern PATout' for larger Dout). Alternatively, in the configuration of FIG. 5D, the filtering configuration MSK1" uses the entire annulus output illumination pattern PATout', but filters it through an "aperture" which comprises a density filter AP1'". For such a configuration, instead of filtering through a mask aperture width, the output illumination pattern PATout' is filtered through a mask density function that is a function of Dout. This density filter function F(Dout) is analogous to the width function Wap" discussed above in reference to FIG. 5C. That is, 360 degrees of the annulus output illumination pattern PATout' is always transmitted, but it is transmitted with a transmission coefficient F(Dout) that depends on diameter, rather than by an "aperture width" that depends on diameter. By analogy with the previous equations, and because the entire output pattern is always transmitted through the filter, for this configuration:

$$Tr=F(Dout)*A(t) \quad \text{(Eq. 15)}$$

In this case F(Dout) defines the proportion of transmission. In such instances, larger F equates to more transmission. With respect to EQUATION 2, and substituting for Tr using EQUATION 15, and for i(t) using EQUATION 1:

$$S(t)=i(t)*Tr=Tr*i(t)=Tr*[Ein/A(t)]=F(Dout)*A(t)*[Ein/A(t)] \quad \text{(Eq. 16)}$$

using K to mean a modified constant of proportionality for Ein, etc., simplifying EQUATION 16, and noting that Dout is a function of time Dout(t):

$$S(t)=K*F(Dout(t)) \quad \text{(Eq. 17)}$$

That is, the output signal S(t) will generally be proportional to the value of the density function at any particular output pattern diameter of the output annulus pattern at that particular time. Such configurations indicate that any density function may be chosen in order to create a particular signal in relation to a particular value of Dout and/or Zfocus. For example, if:

$$F(Dout)=K*Dout \quad \text{(Eq. 18)}$$

and substituting EQUATION 18 into EQUATION 16:

$$S(t)=K*Dout(t) \quad \text{(Eq. 19)}$$

In implementations where Zfocus is at least approximately proportional to Dout, this indicates that:

$$Zfocus(t)=(1/K)*S(t) \quad \text{(Eq. 20)}$$

Thus, for this particular density function for the configuration of FIG. 5D, the signal is proportional to Dout, which indicates that Zfocus(t) is proportional to the signal S(t), which in various implementations may be a convenient configuration for intuitive understanding of the system and for signal processing, etc. It is noted that this result is similar to the result noted above for Wap"=K*Dout² for the configuration of FIG. 5C.

FIG. 8 is a schematic diagram of a first exemplary implementation of a detector signal processing portion 478' (e.g., as one implementation of the detector signal processing portion 478 of FIGS. 4A and 5A). As shown in FIG. 8, the detector signal processing portion 478' includes a latching circuit 810 which receives the focus output signal 478A as a focus monitoring signal (e.g., provided by the focus photodetector PD1 of FIG. 4A or 5A), and receives a latching signal 812, and provides an output signal 479'. In one implementation, the latching signal 812 may correspond to a strobe timing signal (e.g., for the light source 330) that determines a corresponding timing for imaging a surface region of a workpiece 320 in the field of view (FOV) of the imaging configuration. In such an implementation, the strobe timing in the latching signal 812 triggers in the latching circuit 810 a latching of a corresponding focus monitoring signal value, wherein the latched focus monitoring signal value is provided as the output signal 479' and is indicative of the Z-height at the corresponding image exposure timing determined by the strobe timing. FIG. 9 is a schematic diagram of a second exemplary implementation of a detector signal processing portion 478" (e.g., as one implementation of the detector signal processing portion 478 of FIGS. 4A and 5A). As shown in FIG. 9, the detector signal processing portion 478" includes a comparator circuit 910 which receives the focus output signal 478A as a focus monitoring signal (e.g., provided by the focus photodetector PD1 of FIG. 4A or 5A), and receives a reference signal 912, and provides an output signal 479". In one implementation, the reference signal 912 may be related to a focus monitoring signal value that corresponds to a desired Z-height for imaging a surface region of a workpiece 320 in the field of view (FOV) of the imaging configuration. For example, the reference signal 912 may be determined from stored data in the Z-height versus focus monitoring signal calibration portion 373. In operation of the comparator circuit 910, the reference signal 912 triggers a strobe timing on the output signal 479" for a controllable strobe light source (e.g., the light source 330) when the focus modulation of the imaging system as indicated by the focus monitoring signal 478A is at the Z-height that the reference signal 912 is related to.

Figure 10:
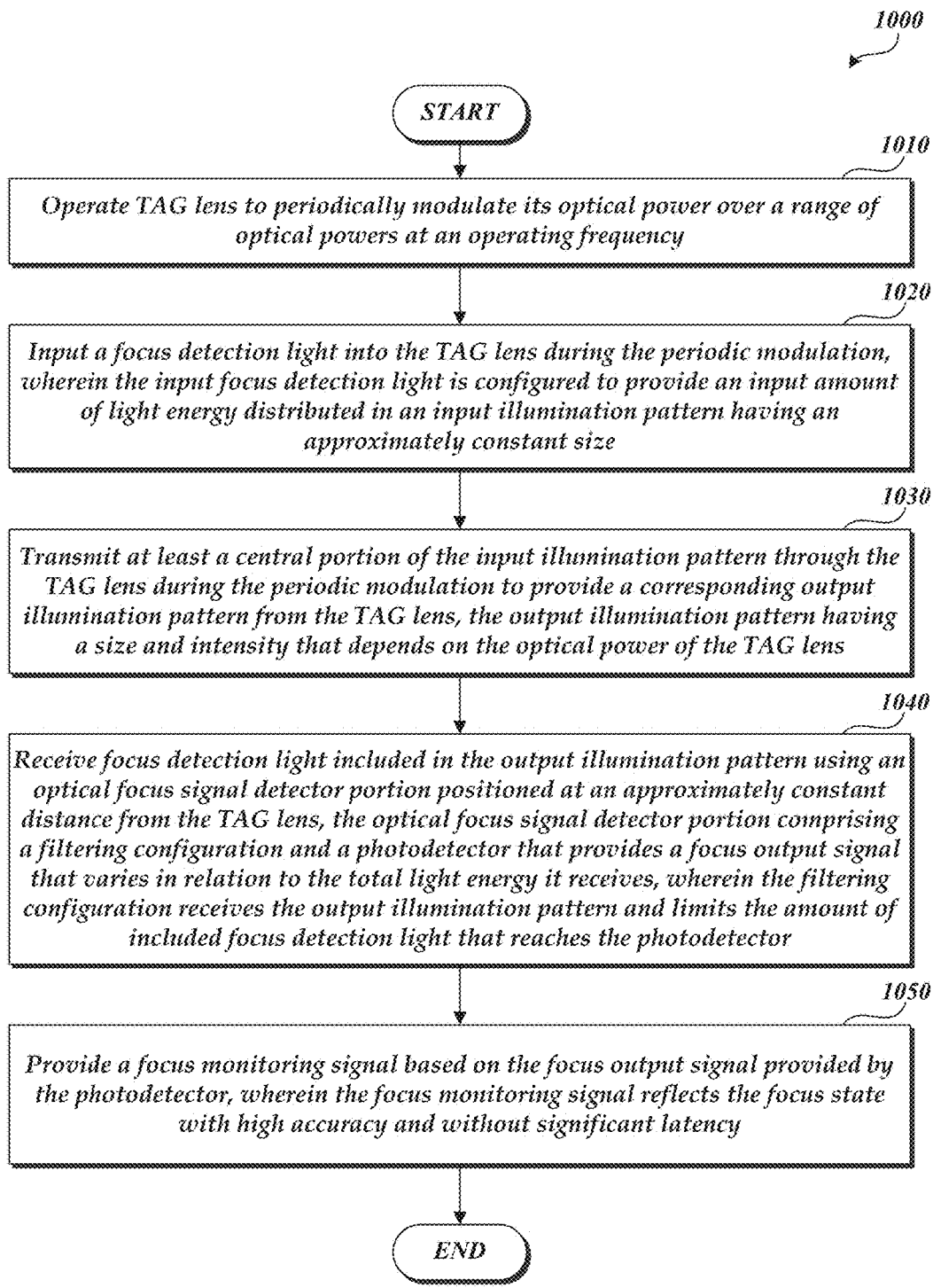
FIG. 10 is a flow diagram illustrating one exemplary implementation of a routine for operating a variable focal length lens system.

FIG. 10 is a flow diagram illustrating one exemplary implementation of a routine 1000 for operating a VFL lens system. At a block 1010, a TAG lens that is part of a VFL system is operated to periodically modulate the TAG lens optical power over a range of optical powers at an operating frequency. At a block 1020, a focus detection light is input into the TAG lens during the periodic modulation, wherein the input focus detection light is configured to provide an input amount of light energy distributed in an input illumination pattern having an approximately constant size. In some embodiments, the input amount of light energy is approximately constant. At a block 1030, at least a central portion of the input illumination pattern is transmitted through the TAG lens during the periodic modulation to provide a corresponding output illumination pattern from the TAG lens, the output illumination pattern having a size and intensity that depends on the optical power of the TAG lens.

At a block 1040, focus detection light included in the output illumination pattern is received using an optical focus signal detector portion positioned at an approximately constant distance from the TAG lens. In various implementations, the optical focus signal detector portion comprises a filtering configuration and a photodetector that provides a focus output signal that varies in relation to the total light energy it receives, wherein the filtering configuration receives the output illumination pattern and limits the amount of included focus detection light that reaches the photodetector. At a block 1050, a focus monitoring signal is provided based on the focus output signal provided by the photodetector, wherein the focus monitoring signal reflects the focus state of the VFL lens system with high accuracy and without significant latency.

While preferred implementations of the present disclosure have been illustrated and described, numerous variations in the illustrated and described arrangements of features and sequences of operations will be apparent to one skilled in the art based on this disclosure. For example, in a number of the examples and embodiments above, the operation is simpler to explain and understand assuming that an approximately constant amount of light energy is distributed in an input illumination pattern having an approximately constant size, in which case the focus output signal (e.g., in an amplified form) may be used as the focus monitoring signal in some embodiments. However, such embodiments are exemplary only, and not limiting. In particular, the embodiment shown in FIG. 6 discloses providing and using a normalization output signal. In such an embodiment, the focus output signal and the normalization output signal may be used in combination to provide a "normalized focus output signal" that may be used as a reliable focus monitoring signal. It is not necessary that the input light energy is constant in such an embodiment. In another alternative embodiment, the focus output signal (or a normalized focus output signal) may be used as a feedback to regulate the light source 330 to keep the focus output signal (or a normalized focus output signal) constant. The light source can typically be regulated at a very high rate (e.g., 5-20 MHz correction rates). In such an embodiment, a focus monitoring signal may be provided based on the level of the light source driving signal that is used to maintain the constant focus output signal.

The foregoing examples illustrate that various alternative forms may be used to implement the principles disclosed herein. In addition, the various implementations described above can be combined to provide further implementations. All of the U.S. patents and U.S. patent applications referred to in this specification are incorporated herein by reference, in their entirety. Aspects of the implementations can be modified, if necessary to employ concepts of the various patents and applications to provide yet further implementations.

These and other changes can be made to the implementations in light of the above-detailed description. In general, in the following claims, the terms used should not be construed to limit the claims to the specific implementations disclosed in the specification and the claims, but should be construed to include all possible implementations along with the full scope of equivalents to which such claims are entitled.

What is claimed is:

1. A variable focal length (VFL) lens system comprising:
a tunable acoustic gradient (TAG) lens operated to periodically modulate its optical power over a range of optical powers at an operating frequency; and
an optical focus monitoring configuration for monitoring a focus state of the VFL lens system, the optical focus monitoring configuration comprising:
a monitoring light source configured to input focus detection light into the TAG lens during the periodic modulation, wherein:
the input focus detection light is configured to provide an input amount of light energy distributed in an input illumination pattern having an approximately constant size; and
at least a central portion of the input illumination pattern is transmitted through the TAG lens during the periodic modulation to provide a corresponding output illumination pattern from the TAG lens, the output illumination pattern having a size and intensity that depends on the optical power of the TAG lens; and
an optical focus signal detector portion positioned at an approximately constant distance from the TAG lens to receive focus detection light included in the output illumination pattern output from the TAG lens, the optical focus signal detector portion comprising a filtering configuration and a focus photodetector that provides a focus output signal that varies in relation to a total light energy that the focus photodetector receives, wherein the filtering configuration receives the output illumination pattern and limits an amount of the included focus detection light that reaches the focus photodetector and a focus monitoring signal is provided based on the focus output signal provided by the focus photodetector.

2. The VFL lens system of claim 1, wherein the focus detection light is at least approximately collimated in the input illumination pattern.

3. The VFL lens system of claim 1, wherein the input illumination pattern is configured such that the corresponding output illumination pattern comprises a solid pattern, and the filtering configuration comprises a spatial filtering aperture that is defined by limits of the focus photodetector, and the solid pattern overfills the focus photodetector at all times during the periodic modulation.

4. The VFL lens system of claim 1, wherein:
the filtering configuration includes a mask comprising a spatially filtering aperture;
the mask blocks a blocked portion of the output illumination pattern at all times during the periodic modulation;
the spatially filtering aperture transmits a transmitted portion of the output illumination pattern at all times; and
the spatially filtering aperture is shaped such that a ratio of the transmitted portion to the blocked portion varies depending on the size of the output illumination pattern.

5. The VFL lens system of claim 4, wherein the input illumination pattern is configured such that the corresponding output illumination pattern comprises an annular pattern.

6. The VFL lens system of claim 1, wherein the filtering configuration includes a mask comprising a density filter having a non-uniform density pattern configured to attenuate the transmission of the output illumination pattern depending on the size of the output illumination pattern.

7. The VFL lens system of claim 6, wherein the density filter is configured to receive and transmit the entire output illumination pattern to the focus photodetector at all times during the periodic modulation.

8. The VFL lens system of claim 6, wherein the input illumination pattern is configured such that the corresponding output illumination pattern comprises an annular pattern, and the non-uniform density pattern is axisymmetric and a density of the non-uniform density pattern varies as a function of radius within the output illumination pattern.

9. The VFL lens system of claim 1, wherein the periodic modulation corresponds to a frequency of at least 50 kHz, the focus monitoring signal comprises a time varying signal that is indicative of the focus state of the TAG lens throughout the modulation period, and the time varying signal is provided with a latency compared to the focus state of not more than 100 nanoseconds.

10. The VFL lens system of claim 1, comprising a controller that operates to drive the TAG lens at a resonant frequency in order to periodically modulate the TAG lens optical power over the range of optical powers at the operating frequency, wherein the focus monitoring signal is input to the controller and is used to adjust at least one of amplitude, frequency, or phase of the periodic modulation of the TAG lens.

11. The VFL lens system of claim 1, further comprising an imaging configuration comprising the TAG lens, an objective lens, and a camera portion, wherein:
the objective lens inputs workpiece light from an imaged surface region of a workpiece in a field of view (FOV) of the imaging configuration and transmits the workpiece light through the TAG lens, and the camera portion receives the workpiece light from the TAG lens and provides an image exposure such that it is focused at a corresponding imaging system focal plane having at least one of a focus distance or Z-height relative to the imaging configuration;
at least one of the focus distance or Z-height of the imaging system focal plane is controlled by the TAG lens optical power; and
the focus monitoring signal is indicative of at least one of the focus distance or Z-height of the imaging system focal plane.

12. The VFL lens system of claim 11, wherein the VFL lens system includes calibration data that relates respective focus distances or Z-heights to respective focus monitoring signal values.

13. The VFL lens system of claim 11, wherein:
the VFL lens system is configured to control the image exposure using an image exposure timing that determines the corresponding imaging system focal plane; and
the VFL lens system is configured to control at least one of a timing of a controllable strobe light source that is included in the VFL lens system or a timing of a controllable image integration period of the camera portion, to provide the image exposure timing.

14. The VFL lens system of claim 13, further comprising a latching circuit configured to latch a focus monitoring signal value at a time corresponding to the image exposure timing, wherein the latched focus monitoring signal value is indicative of the focus distance or Z-height for the corresponding image exposure.

15. The VFL lens system of claim 13, further comprising a comparator circuit configured to input the focus monitoring signal and input a reference signal related to a desired imaging focus distance or Z-height, and output a trigger signal that controls the image exposure timing to occur when the focus monitoring signal corresponds to the reference signal.

16. The VFL lens system of claim 11, wherein the monitoring light source is configured to provide focus detection light consisting of a first set of wavelengths in the input illumination pattern, and the optical focus monitoring configuration further comprises:
a first beamsplitter that is located between the objective lens and the TAG lens and receives focus detection light from the monitoring light source and directs the input illumination pattern to pass through the TAG lens along with the workpiece light; and
a second beamsplitter that is located between the TAG lens and the camera portion wherein the second beamsplitter is configured to receive the output illumination pattern from the TAG lens along with the workpiece light and reflect the first set of wavelengths included in the output illumination pattern toward the optical focus signal detector portion and transmit other wavelengths included in the workpiece light to the camera portion.

17. The VFL lens system of claim 1, wherein:
the optical focus monitoring configuration further comprises a beamsplitter that directs a first split output illumination pattern to the optical focus signal detector portion and directs a second split output illumination pattern to a normalization optical detector configured to transmit the entire second split output illumination pattern to a normalization photodetector that provides a normalization output signal that varies in relation to the total light energy that the normalization photodetector receives; and
the VFL lens system further comprises a focus monitoring output circuit that is configured to input the focus output signal and the normalization output signal and to produce a normalized focus monitoring signal, wherein variations in the focus output signal due to variations in the total light energy included in the output illumination pattern are compensated based on the normalization output signal.

18. The VFL lens system of claim 1, wherein the monitoring light source comprises a pattern generator that determines a shape for the input illumination pattern that is input into the TAG lens, resulting in a corresponding shape for the output illumination pattern from the TAG lens.

19. The VFL lens system of claim 1, wherein the input amount of light energy distributed in the input illumination pattern is approximately constant.

20. A method for optically monitoring a focus state of a variable focal length (VFL) lens system comprising a tunable acoustic gradient (TAG) lens, in order to provide a focus monitoring signal that reflects the focus state with high accuracy and without significant latency, the method comprising:
   operating the TAG lens to periodically modulate its optical power over a range of optical powers at an operating frequency;
   inputting a focus detection light into the TAG lens during the periodic modulation, wherein the input focus detection light is configured to provide an input amount of light energy distributed in an input illumination pattern having an approximately constant size;
   transmitting at least a central portion of the input illumination pattern through the TAG lens during the periodic modulation to provide a corresponding output illumination pattern from the TAG lens, the output illumination pattern having a size and intensity that depends on the optical power of the TAG lens;
   receiving focus detection light included in the output illumination pattern using an optical focus signal detector portion positioned at an approximately constant distance from the TAG lens, the optical focus signal detector portion comprising a filtering configuration and a photodetector that provides a focus output signal that varies in relation to the total light energy it receives, wherein the filtering configuration receives the output illumination pattern and limits the amount of included focus detection light that reaches the photodetector; and
   providing a focus monitoring signal based on the focus output signal provided by the photodetector.

21. The method of claim 20, wherein the focus detection light is at least approximately collimated in the input illumination pattern.

22. The method of claim 20, wherein:
   the filtering configuration includes a mask comprising a spatially filtering aperture;
   the mask blocks a blocked portion of the output illumination pattern at all times during the periodic modulation;
   the spatially filtering aperture transmits a transmitted portion of the output illumination pattern at all times; and
   the spatially filtering aperture is shaped such that a ratio of the transmitted portion to the blocked portion varies depending on the size of the output illumination pattern.

23. The method of claim 20, wherein the filtering configuration includes a mask comprising a density filter having a non-uniform density pattern configured to attenuate the transmission of the output illumination pattern depending on the size of the output illumination pattern.

24. The method of claim 20, wherein the periodic modulation corresponds to a frequency of at least 50 kHz, the focus monitoring signal comprises a time varying signal that is indicative of the focus state of the TAG lens throughout the modulation period and the time varying signal is provided with a latency compared to the focus state of not more than 100 nanoseconds.

25. The method of claim 20, wherein:
   the VFL lens system further comprises an imaging configuration comprising the TAG lens, an objective lens, and a camera portion;
   the objective lens inputs workpiece light from an imaged surface region of a workpiece in a field of view (FOV) of the imaging configuration and transmits the workpiece light through the TAG lens, and the camera portion receives the workpiece light from the TAG lens and provides an image focused at an imaging system focal plane having at least one of a focus distance or Z-height relative to the imaging configuration;
   at least one of the focus distance or Z-height of the imaging system focal plane is controlled by the TAG lens optical power; and
   the focus monitoring signal is indicative of at least one of the focus distance or Z-height of the imaging system focal plane.

* * * * *